United States Patent

Schumacher

Patent Number: 6,080,858
Date of Patent: Jun. 27, 2000

[54] PROCESS FOR REACTING FLUORINE-SUBSTITUTED HETEROCYCLES WITH AMINES IN THE PRESENCE OF PHASE TRANSFER CATALYSTS

[75] Inventor: Christian Schumacher, Kelkheim, Germany

[73] Assignee: DyStar Textilfarben GmbH & Co. Deutschland KG, Germany

[21] Appl. No.: 09/172,364

[22] Filed: Oct. 14, 1998

[30] Foreign Application Priority Data

Nov. 15, 1997 [DE] Germany .............. 197 507 01

[51] Int. Cl.$^7$ .............. C07D 265/36; C07D 251/18
[52] U.S. Cl. .............. 544/99; 544/208
[58] Field of Search .............. 544/99, 208

[56] References Cited

U.S. PATENT DOCUMENTS

| | | | |
|---|---|---|---|
| 4,189,570 | 2/1980 | Bonometti et al. | 544/211 |
| 4,189,576 | 2/1980 | Altorfer et al. | 544/211 |
| 5,440,039 | 8/1995 | Frosch et al. | 544/211 |

FOREIGN PATENT DOCUMENTS 4416017   5/1994   Germany .

*Primary Examiner*—Joseph K. McKane
*Attorney, Agent, or Firm*—Connolly, Bove, Lodge & Hutz, LLP

[57] ABSTRACT

Process for reacting fluorine-substituted heterocycles with amines in the presence of phase transfer catalysts The reaction of an amino compound with a fluorine-substituted triazine or pyrimidine group is carried out in the presence of a phase transfer catalyst, preferably of the formula (4a), (4b) or (4c)

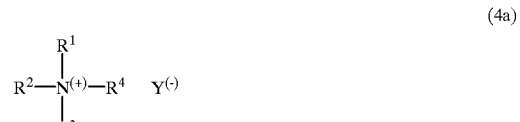

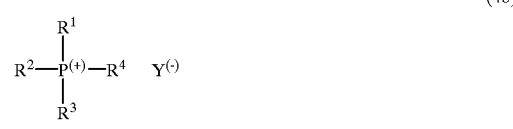

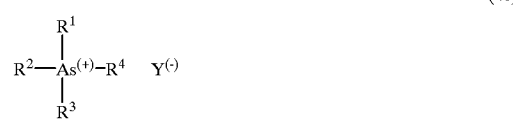

where $R^1$, $R^2$, $R^3$ and $R^4$ are identical or different and are each alkyl having from 1 to 20 carbon atoms which may be substituted by phenyl, or are phenyl.

16 Claims, No Drawings

PROCESS FOR REACTING FLUORINE-SUBSTITUTED HETEROCYCLES WITH AMINES IN THE PRESENCE OF PHASE TRANSFER CATALYSTS

Process for reacting fluorine-substituted heterocycles with amines in the presence of phase transfer catalysts The reaction of amino compounds with fluorine-substituted triazine and pyrimidine compounds has been known for a long time and has been described many times in the literature, for example particularly in the preparation of dyes which have a fluorine-substituted triazine or pyrimidine group as fiber-reactive component or in the preparation of their fluorotriazine- or fluoropyrimidine-containing precursors or intermediates (see, for example, DE-A44 16 017 and U.S. Pat. Nos. 4,189,570, 4,189,576 and 5,440,039). The methods are either too technically complicated or the yields and the quality of the products obtained in these reactions by replacement of a fluorine atom of the triazine or pyrimidine by the amino group of an amino-containing dye or a precursor thereof are unsatisfactory. Methods of reacting amino compounds with fluorine-substituted heterocycles were thus in need of improvement.

It has now surprisingly been found that yields and purity of the products obtained can be significantly improved by use of phase transfer catalysts.

The present invention accordingly provides a process for preparing compounds of the formula (1a) or (1b) or (1c)

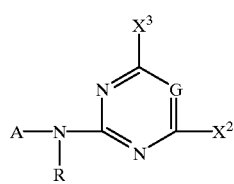

(1a)

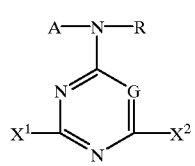

(1b)

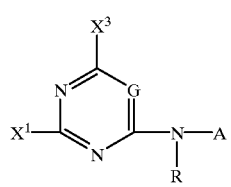

(1c)

where
A is phenyl or phenyl substituted by 1 or 2 substituents selected from the group consisting of sulfo, carboxy, alkyl having from 1 to 4 carbon atoms, e.g. methyl or ethyl, alkoxy having from 1 to 4 carbon atoms, e.g. methoxy or ethoxy, chlorine, bromine, amino, alkylamino having from 1 to 4 carbon atoms in the alkyl group, sulfamoyl, carbamoyl and a fiber-reactive group from the vinyl sulfone series, e.g. β-sulfatoethylsulfonyl, vinylsulfonyl and β-chloroethylsulfonyl, said fiber-reactive group being bound directly by a covalent bond or via an alkylene group having from 1 to 4 carbon atoms or an alkylene-oxy-alkylene group having a total of 2 to 6 carbon atoms to the aromatic radical, or is trisulfonaphthyl or naphthyl or naphthyl substituted by 1 or 2 substituents selected from the group consisting of sulfo, carboxy, alkyl having from 1 to 4 carbon atoms, e.g. methyl or ethyl, alkoxy having from 1 to 4 carbon atoms, e.g. methoxy or ethoxy, amino, alkylamino having from 1 to 4 carbon atoms in the alkyl group, sulfamoyl, carbamoyl and a fiber-reactive group from the vinyl sulfone series, e.g. β-sulfatoethylsulfonyl, vinylsulfonyl and β-chloroethylsulfonyl, said fiber-reactive group being bound directly by a covalent bond or via an alkylene group having from 1 to 4 carbon atoms or an alkylene-oxy-alkylene group having a total of 2 to 6 carbon atoms to the aromatic radical, or is the radical of a dye chromophore which may contain a further amino group and is selected from the group consisting of monoazo, disazo, copper, chromium and cobalt complex monoazo and disazo, anthraquinone, azomethine, phenazine, stilbene, triphenylmethane, xanthene, thioxanthene, nitroaryl, naphthoquinone, pyrenequinone, perylenetetracarbimide, formazane, copper formazane, phthalocyanine, copper phthalocyanine, nickel phthalocyanine, cobalt phthalocyanine, dioxazine or triphendioxazine dyes, R is hydrogen or alkyl having from 1 to 4 carbon atoms, e.g. methyl or ethyl, G is an N atom or a group of the formula (a)

(a)

where $R^0$ is hydrogen, halogen, e.g. chlorine or fluorine, or cyano, $X^1$ is hydrogen, halogen, e.g. chlorine or fluorine, or a group of the formula (b)

(b)

where $R^a$ has one of the meanings of R and $A^0$ has one of the meanings of A and is preferably fluorine, $X^2$ has one of the meanings of $X^1$ and $X^3$ has one of the meanings of $X^1$, by reacting an amino compound of the formula (2)

(2)

where A and R are as defined above, with a compound of the formula (3)

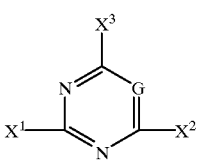

(3)

where G, $X^1$, $X^2$ and $X^3$ are as defined above and at least one of $X^1$, $X^2$ and $X^3$ is fluorine, wherein the reaction is carried out in water or a mixture of water with an organic solvent which is immiscible or only partially miscible with water, in the presence of a phase transfer catalyst in an amount of from 0.1 to 10 mol %, preferably from 0.3 to 5 mol %, based on the starting compound of the formula (2).

The reaction is generally carried out at a temperature of from 0° C. to 80° C. and at a pH of from 2 to 10, preferably from 4 to 8.

In the reaction medium, the volume ratio of water to the organic solvent is in the range from 100:0 to 50:50, preferably in the range from 100:0 to 20:80.

Suitable organic solvents are, if they are partially miscible with water, those which can be mixed with water or dissolved in water in a proportion of at most 10% by weight.

Examples of organic solvents are aromatic hydrocarbons such as benzene, toluene, xylene, chlorobenzene or dichlorobenzene, or chlorinated aliphatic hydrocarbons such as carbon tetrachloride, dichloromethane or chloroform.

Phase transfer catalysts which can be used according to the invention are, for example, compounds of the formula (4a), (4b) or (4c)

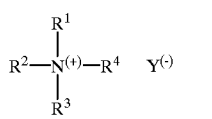
(4a)

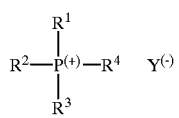
(4b)

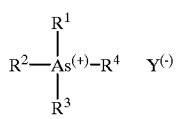
(4c)

where $R^1$, $R^2$, $R^3$ and $R^4$ are identical or different and are each alkyl having from 1 to 20 carbon atoms, preferably from 1 to 10 carbon atoms, which can be substituted by phenyl, or are phenyl, for example methyl, ethyl, propyl, n-butyl, n-octyl, n-decyl, n-dodecyl, n-octadecyl or benzyl, and $Y^{(-)}$ is an anion such as a halide anion, e.g. a chloride or bromide anion, or a chlorate, benzoate, p-nitrobenzoate, phenylsulfonate or naphthylsulfonate anion. Examples of such phase transfer catalysts are trimethyl-n-hexadecylammonium, trimethyl-n-pentadecylammonium, tri-methyl-n-tetradecylammonium, triethyl-n-dodecylammonium, triethyl-n-decylammonium, tri(n-propyl)-n-decylammonium, tri(n-butyl)-n-decyl-ammonium, tetra(n-butyl)ammonium, tetra(n-hexyl) ammonium, tetra-(n-pentyl)ammonium, tetra(n-octyl) ammonium and trimethylbenzyl-ammonium chloride and bromide and also tetraphenylphosphonium bromide and tetraphenylarsonium bromide. Examples of further phase transfer catalysts apart from those just mentioned are described in Dehmlow/Dehmlow, Phase Transfer Catalysis, 2nd edition, Verlag Chemie, pages 43, 45, 49.

Examples of starting compounds of the formula (2) are aniline and naphthylamine derivatives which can be substituted in the aromatic ring by the substituents mentioned for formula (2), for example sulfo, carboxy, alkyl having from 1 to 4 carbon atoms, alkoxy having from 1 to 4 carbon atoms, chlorine, bromine, sulfamoyl and/or a fiber-reactive group of the vinyl sulfone series. Many amino-containing dye chromophores and derivatives of such compounds are described in the literature concerning dye chemistry.

Examples of compounds of the formula (3) are 2,4,6-trifluoro-1,3,5-triazine, 2,4,6-trifluoropyrimidine and 5-chloro-2,4,6-trifluoropyrimidine.

The process of the invention can be employed particularly advantageously for amino-containing dye chromophores which are difficult to acylate, i.e. react with halogen-substituted heterocycles. Such dye chromophores are, for example, diamino-triphendioxazine compounds suitable as intermediates for triphendioxazine dyes, such as a compound of the formula (A), and also compounds of the general formula (B)

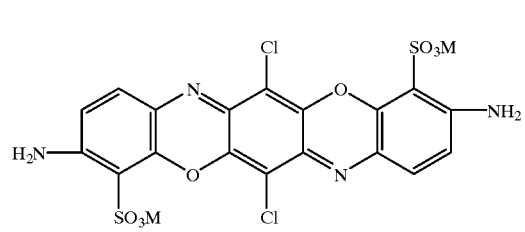
(A)

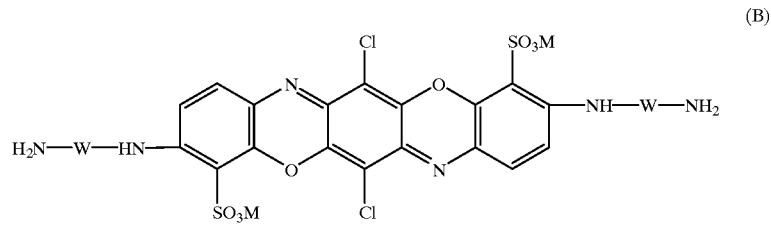
(B)

where M is hydrogen or an alkali metal such as sodium, potassium or lithium, and W is alkylene having from 2 to 6 carbon atoms or phenylene which can be substituted by 1 or 2 sulfo groups and possibly a further customary substituent such as alkyl having from 1 to 4 carbon atoms, e.g. methyl or ethyl, alkoxy having from 1 to 4 carbon atoms, e.g. methoxy or ethoxy, carboxy or chlorine, and furthermore the leuco form of those diamino-triphendioxazine compounds as described, for ex., in European Patent Application No. 0 773 264, such as a compound of the formula (A-1)

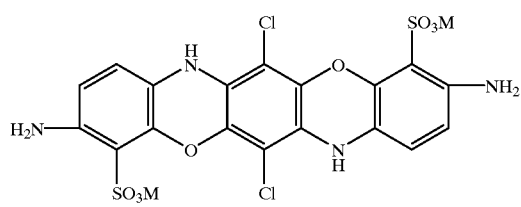

(A-1)

The abovementioned names of the groups "sulfato", "sulfo" and "carboxy" refer to groups of the formulae —OSO$_3$M, —SO$_3$M or —COOM, where M is as defined above.

The following Examples illustrate the invention. Parts and percentages are by weight, unless indicated otherwise. Parts by weight bear the same relationship to parts by volume as that of the kilogram to the liter. The compounds described by means of formulae in the Examples are shown in the form of the free acids; in general, they are used in the reaction in the form of their alkali metal salts, e.g. lithium, sodium or potassium salts, or prepared and isolated as such.

EXAMPLE 1

10.9 parts of the compound of the formula

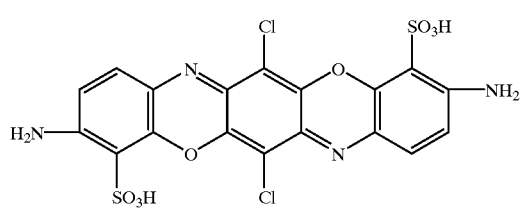

are dissolved in 500 parts of water at 25° C. and a pH of 7 by means of an aqueous lithium hydroxide solution. 67.5 parts of sodium dithionite are then added thereto and the reduction is carried out under a nitrogen atmosphere at 40° C. and a pH of 7. 0.5 parts of methyltri(n-octyl)ammonium chloride and then 13.3 parts of 2,4,5-trifluoropyrimidine are added to the resulting solution of the leuco form of the triphendioxazine dye base used (cf. EP-A-0 773 264, Example 1), the reaction mixture is heated to 60° C. and the reaction is completed while maintaining a pH of 7 by means of an aqueous lithium hydroxide solution.

This gives the compound of the formula

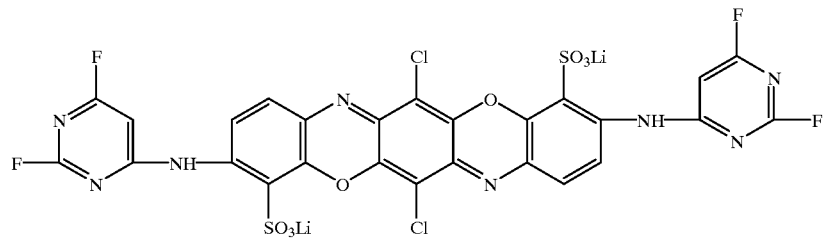

which is isolated as the sodium salt in a customary manner by salting out using sodium chloride.

The yield is 88% of theory, based on the triphendioxazine dye base. If this reaction is carried out without the phase transfer catalyst, the yield is only 35% of theory; a yield comparable to that obtained according to the invention is obtained without catalyst only when a considerable excess of the trifluoropyrimidine, e.g. a 10-fold molar excess, is used in place of the 2.5-fold molar excess employed here in the process of the invention.

EXAMPLE 2

0.1 mol of aniline-2-sulfonic acid are dissolved in 500 ml of water at a pH of 6 by means of lithium hydroxide. 0.05 mol of sodium fluoride and subsequently 0.0025 mol of methyltri(n-octyl)ammonium chloride are added thereto and this mixture is subsequently admixed while stirring vigorously with 0.11 mol of 2,4,6-trifluoro-1,3,5-triazine. The mixture is stirred further for about 10 minutes and an aqueous solution of 0.1 mol of 2,4-diaminobenzenesulfonic acid having a pH of 6 is then added thereto, the mixture is stirred further for about one hour at a pH of 6 and a temperature of 25° C., and the resulting compound of the formula

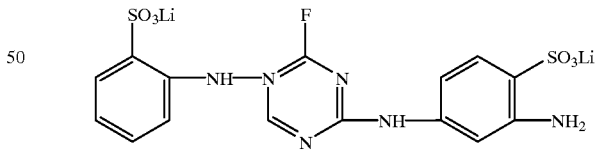

is then isolated in a yield of 82% of theory and a purity of 93%. This compound can also be used directly in the form of the aqueous synthesis solution obtained without isolation in a customary synthesis of a dye, for example as diazo or coupling component.

If the above-described reaction according to the invention is carried out without use of the catalyst, the product is obtained in a purity of only 82%.

I claim:

1. A process for preparing a compound of the formula (1a) or (1b) or (1c)

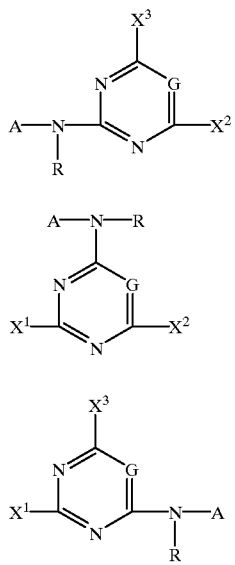

where

A is phenyl or phenyl substituted by 1 or 2 substituents selected from the group consisting of sulfo, carboxy, alkyl having from 1 to 4 carbon atoms, alkoxy having from 1 to 4 carbon atoms, chlorine, bromine, amino, alkylamino having from 1 to 4 carbon atoms in the alkyl group, sulfamoyl, carbamoyl and a fiber-reactive group from the vinyl sulfone series, said fiber-reactive group being bound directly by a covalent bond or via an alkylene group having from 1 to 4 carbon atoms or an alkylene-oxy-alkylene group having a total of 2 to 6 carbon atoms to the aromatic radical, or is trisulfonaphthyl or naphthyl or naphthyl substituted by 1 or 2 substituents selected from the group consisting of sulfo, carboxy, alkyl having from 1 to 4 carbon atoms, alkoxy having from 1 to 4 carbon atoms, amino, alkylamino having from 1 to 4 carbon atoms in the alkyl group, sulfamoyl, carbamoyl and a fiber-reactive group from the vinyl sulfone series, said fiber-reactive group being bound directly by a covalent bond or via an alkylene group having from 1 to 4 carbon atoms or an alkylene-oxy-alkylene group having a total of 2 to 6 carbon atoms to the aromatic-radical, or is the radical of a dye chromophore optionally containing a further amino group, which is selected from the group consisting of monoazo, disazo, copper, chromium and cobalt complex monoazo and disazo, anthraquinone, azomethine, phenazine, stilbene, triphenylmethane, xanthene, thioxanthene, nitroaryl, naphthoquinone, pyrenequinone, perylenetetracarbimide, formazane, copper formazane, phthalocyanine, copper phthalocyanine, nickel phthalocyanine, cobalt phthalocyanine, dioxazine or triphendioxazine dyes, R is hydrogen or alkyl having from 1 to 4 carbon atoms, G is an N atom or a group of the formula (a)

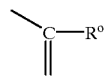

where $R^o$ is hydrogen, halogen or cyano, $X^1$ is hydrogen, halogen or a group of the formula (b)

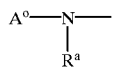

where $R^a$ has one of the meanings of R and $A^o$ has one of the meanings of A, $X^2$ has one of the meanings of $X^1$ and $X^3$ has one of the meanings of $X^1$, by reacting an amino compound of the formula (2)

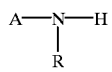

where A and R are as defined above, with a compound of the formula (3)

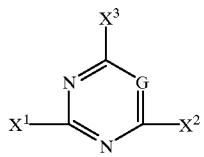

where G, $X^1$, $X^2$ and $X^3$ are as defined above and at least one of $X^1$, $X^2$ and $X^3$ is fluorine, wherein the reaction is carried out in water or a mixture of water with an organic solvent which is immiscible or only partially miscible with water, in the presence of a phase transfer catalyst in an amount of from 0.1 to 10 mol %, based on the starting compound of the formula (2).

2. The process as claimed in claim 1, wherein the volume ratio of water to the organic solvent is in the range from 100:0 to 50:50.

3. The process as claimed in claim 1, wherein the phase transfer catalyst is a compound of the formula (4a)

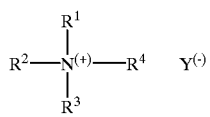

where $R^1$, $R^2$, $R^3$ and $R^4$ are identical or different and are each phenyl or alkyl having from 1 to 20 carbon atoms unsubstituted or substituted by phenyl, and $Y^{(-)}$ is an anion.

4. The process as claimed in claim 2, wherein the phase transfer catalyst is a compound of the formula (4a)

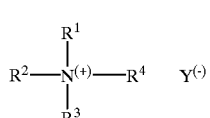

where $R^1$, $R^2$, $R^3$ and $R^4$ are identical or different and are each phenyl or alkyl having from 1 to 20 carbon atoms unsubstituted or substituted by phenyl, and $Y^{(-)}$ is an anion.

5. The process as claimed in claim 1, wherein the phase transfer catalyst is a compound of the formula (4b) or (4c)

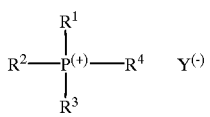
(4b)

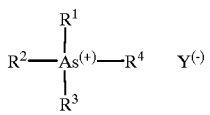
(4c)

where R¹, R², R³ and R⁴ are identical or different and are each phenyl or alkyl having from 1 to 20 carbon atoms which may be substituted by phenyl, and $Y^{(-)}$ is an anion.

6. The process as claimed in claim 2, wherein the phase transfer catalyst is a compound of the formula (4b) or (4c)

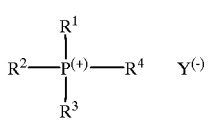
(4b)

-continued

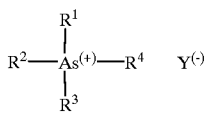
(4c)

where R¹, R², R³ and R⁴ are identical or different and are each phenyl or alkyl having from 1 to 20 carbon atoms which may be substituted by phenyl, and $Y^{(-)}$ is an anion.

7. The process as claimed in claim 3, wherein R¹, R², R³ and R⁴ are identical or different and are each alkyl having from 1 to 10 carbon atoms.

8. The process as claimed in claim 4, wherein R¹, R², R³ and R⁴ are identical or different and are each alkyl having from 1 to 10 carbon atoms.

9. The process as claimed in claim 5, wherein R¹, R², R³ and R⁴ are identical or different and are each alkyl having from 1 to 10 carbon atoms.

10. The process as claimed in claim 6, wherein R¹, R², R³ and R⁴ are identical or different and are each alkyl having from 1 to 10 carbon atoms.

11. The process as claimed in claim 1, wherein the starting compound of the formula (2) is a compound of the formula (A) or its leuco form or a compound of the formula (B)

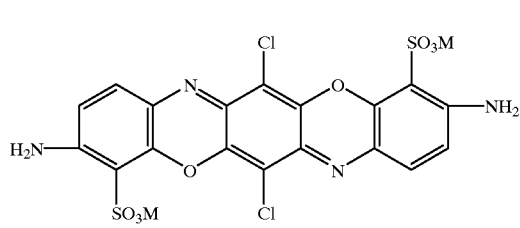
(A)

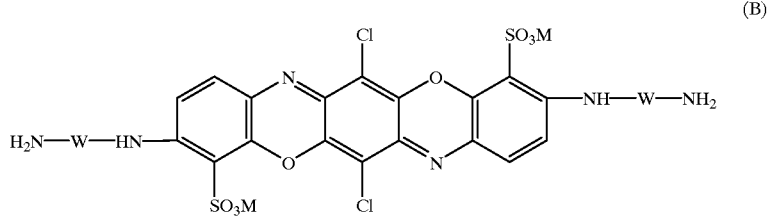
(B)

where M is hydrogen or an alkali metal and W is alkylene having from 2 to 6 carbon atoms, phenylene or phenylene substituted by 1 or 2 sulfo groups and, optionally a further substituent.

12. The process as claimed in claim 2, wherein the starting compound of the formula (2) is a compound of the formula (A) or its leuco form or a compound of the formula (B)

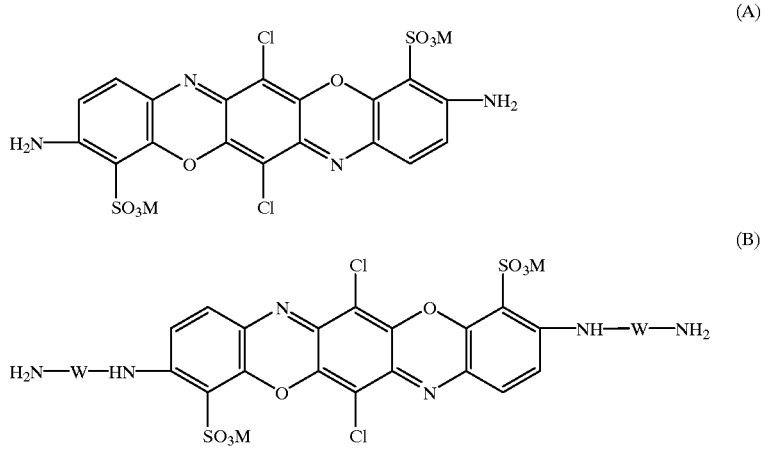

(A)

(B)

where M is hydrogen or an alkali metal and W is alkylene having from 2 to 6 carbon atoms, phenylene or phenylene substituted by 1 or 2 sulfo groups and, optionally a further substituent.

13. The process as claimed in claim 3, wherein the starting compound of the formula (2) is a compound of the formula (A) or its leuco form or a compound of the formula (B)

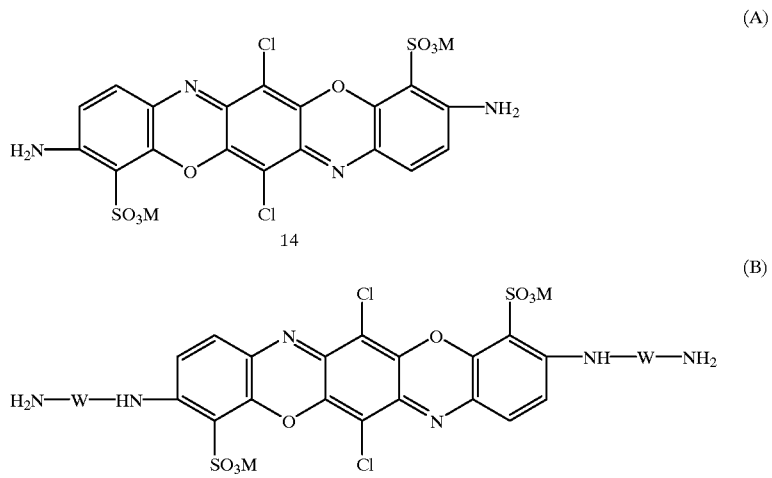

(A)

(B)

where M is hydrogen or an alkali metal and W is alkylene having from 2 to 6 carbon atoms, phenylene or phenylene substituted by 1 or 2 sulfo groups, and optionally a further substituent.

14. The process as claimed in claim 11, wherein W is an alkylene having from 2 to 6 carbon atoms, phenylene or phenylene substituted by 1 or 2 sulfo groups and a further substituent selected from the group consisting of an alkyl of 1 to 4 carbon atoms, alkoxy of 1 to 4 carbon atoms, carboxy and chlorine.

15. The process as claimed in claim 12, wherein W is an alkylene having from 2 to 6 carbon atoms, phenylene or phenylene substituted by 1 or 2 sulfo groups and a further substituent selected from the group consisting of an alkyl of 1 to 4 carbon atoms, alkoxy of 1 to 4 carbon atoms, carboxy and chlorine.

16. The process as claimed in claim 13, W is an alkylene having from 2 to 6 carbon atoms, phenylene or phenylene substituted by 1 or 2 sulfo groups and a further substituent selected from the group consisting of an alkyl of 1 to 4 carbon atoms, alkoxy of 1 to 4 carbon atoms, carboxy and chlorine.

* * * * *